United States Patent
Rocci et al.

(10) Patent No.: US 11,278,334 B2
(45) Date of Patent: Mar. 22, 2022

(54) VARIABLE ANGLE BONE SCREW HAVING A HARDENED HEAD

(71) Applicant: DePuy Synthes Products, Inc., Raynham, MA (US)

(72) Inventors: Mirko Rocci, Bettlach (CH); This Aebi, Grenchen (CH); Joel Oberli, Niederdorf (CH); Johanna F. Menze, Zürich (CH); Said Ghammar, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 232 days.

(21) Appl. No.: 16/419,507

(22) Filed: May 22, 2019

(65) Prior Publication Data

US 2020/0367951 A1   Nov. 26, 2020

(51) Int. Cl.
*A61B 17/86* (2006.01)
*A61B 17/80* (2006.01)

(52) U.S. Cl.
CPC ...... *A61B 17/8605* (2013.01); *A61B 17/8057* (2013.01); *A61B 17/8625* (2013.01); *A61B 17/866* (2013.01); *A61B 2017/8655* (2013.01)

(58) Field of Classification Search
CPC ............ A61B 17/8685; A61B 17/8625; A61B 17/8605
See application file for complete search history.

(56) References Cited

U.S. PATENT DOCUMENTS

| | | | |
|---|---|---|---|
| 6,666,868 B2 | 12/2003 | Fallin | |
| 6,916,321 B2 | 7/2005 | Tenhuisen et al. | |
| 7,220,263 B2 | 5/2007 | Cordaro | |
| 7,794,483 B2 | 9/2010 | Capanni | |
| 8,114,141 B2 | 2/2012 | Appenzeller et al. | |
| 8,574,268 B2 | 11/2013 | Chan et al. | |
| 9,265,542 B2 | 2/2016 | Koay et al. | |
| 9,277,947 B2 | 3/2016 | Koay et al. | |
| 9,388,842 B2 | 7/2016 | Dawson et al. | |
| 9,566,098 B2 | 2/2017 | Dunn et al. | |
| 2007/0173845 A1 | 7/2007 | Kim | |
| 2009/0157123 A1* | 6/2009 | Appenzeller | A61B 17/686 606/301 |
| 2011/0106172 A1 | 5/2011 | Wallenstein et al. | |
| 2011/0257689 A1 | 10/2011 | Fiechter et al. | |
| 2013/0245697 A1 | 9/2013 | Hulliger | |

FOREIGN PATENT DOCUMENTS

| | | |
|---|---|---|
| EP | 2676621 | 12/2013 |
| EP | 3162313 | 5/2017 |

OTHER PUBLICATIONS

Filed Mar. 20, 2018, entitled Bone Plate With Form-Fitting Variable-Angle Locking Hole, U.S. Appl. No. 15/926,390.

\* cited by examiner

*Primary Examiner* — Olivia C Chang
(74) *Attorney, Agent, or Firm* — BakerHostetler

(57) ABSTRACT

A variable angle bone screw includes a first portion and a second portion that is separate from the first portion and configured to be attached to the first portion. The first portion defines at least a portion up to an entirety of the threaded head of the variable angle bone screw. The second portion defines at least a portion up to an entirety of the threaded shaft of the variable angle bone screw. The threaded head can have a first material hardness, and the threaded shaft can have a second material hardness that is less than the first material hardness.

16 Claims, 9 Drawing Sheets

VARIABLE ANGLE BONE SCREW HAVING A HARDENED HEAD

BACKGROUND

When bones are damaged through trauma, disease, distraction osteogenesis, or orthognathic surgery, the defect is typically reduced, and bone fixation plates are commonly applied to the bone on sides of the defect to ensure union in the desired position. Bone screws can be sized to be driven through respective fixation holes of the plate and into the underlying bone to secure the bone plate to the bone. One common bone screw used in such application is generally referred to as a compression screw. Compression screws have unthreaded heads and threaded shafts. Accordingly, the compression screw can be driven through the plate fixation hole and into the underlying bone until the head applies a compression force against the bone plate toward the underlying bone. Another common bone screw used in such applications is generally referred to as a locking screw. Locking screws have threaded heads and threaded shafts. The threaded heads purchase with the plate inside the fixation holes to reach a stable construct, able to transfer bending moments over the screw head/plate hole interface and to avoid loosening or backing out of the screws. In particular, the locking screw can be driven through the plate fixation hole and into the underlying bone until the head threadedly mates with the bone plate in the fixation hole. The threaded heads of locking screws typically do not apply a compressive force against the bone plate toward the underlying bone.

Conventionally, locking screws were inserted through the screw hole along the central screw hole axis in order to ensure that the threaded screw head mates with the plate in the threaded fixation hole. Locking screws can include standard-type locking screws and variable-angle (VA) screws. Standard-type locking screws are configured to lock within a bone fixation hole substantially only at a "nominal" orientation whereby the central screw axis is substantially coincident with the central hole axis. Variable-angle locking screws are configured to threadedly mate with a threaded bone plate in a variable angle hole of the bone plate so as to selectively lock to the bone plate at an angle within a range of permissible angles with respect to the central axis of the variable angle hole.

SUMMARY

According to one example of the present disclosure, a variable angle bone screw includes a first portion that defines at least a portion of a head having at least one external thread configured to mate with a thread of a variable angle locking hole of a bone plate. The variable angle bone screw further includes a second portion that is separate from the first portion and attached to the first portion. The second portion defines at least a portion of a shaft having at least one thread configured to purchase with bone. The at least one thread of the first portion has a first material hardness, and the at least one thread of the second portion has a second material hardness that can be less than the first material hardness.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings.

DETAILED DESCRIPTION

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include "at least one" and the plural. Further, reference to a plural as used in the specification including the appended claims includes the singular "a," "an," and "one," and further includes "at least one." Further still, reference to a particular numerical value in the specification including the appended claims includes at least that particular value, unless the context clearly dictates otherwise.

The term "plurality", as used herein, means more than one. When a range of values is expressed, another example includes from the one particular value and/or to the other particular value. Similarly, when values are expressed as approximations, by use of the antecedent "about," it will be understood that the particular value forms another example. All ranges are inclusive and combinable.

The terms "approximately" and "substantially" as used herein with respect to various sizes, shapes, dimensions, or other parameter can include the states size, shape, dimension, or other parameter and 10% greater than or less than the stated size, shape, dimension, or other parameter. Further, the terms "approximately" and "substantially" can equally apply to the specific value, shape, or direction of the structure as stated.

When variable angle (VA) locking screws are angulated and threadedly locked to a bone plate, the VA locking screws can achieve high cantilever strengths when the plate thread undergoes a smooth deformation. Further, it can be desirable to reduce or prevent the thread of the VA screw from undergoing deformation when the VA screw is threadedly mated to the bone plate. Both objectives can be met by providing a VA screw whose threaded head has a material hardness greater than the shaft. However, increasing the hardness of conventional VA screws has been found to reduce the fatigue strength of the shaft, particularly in the case of titanium screws. While a masking process could be used to selectively harden the head of the VA screws, this is a time consuming manual process. Accordingly, two-piece VA screws are described herein having a threaded VA head having a greater hardness than the VA shaft.

Figures 1A, 1B:
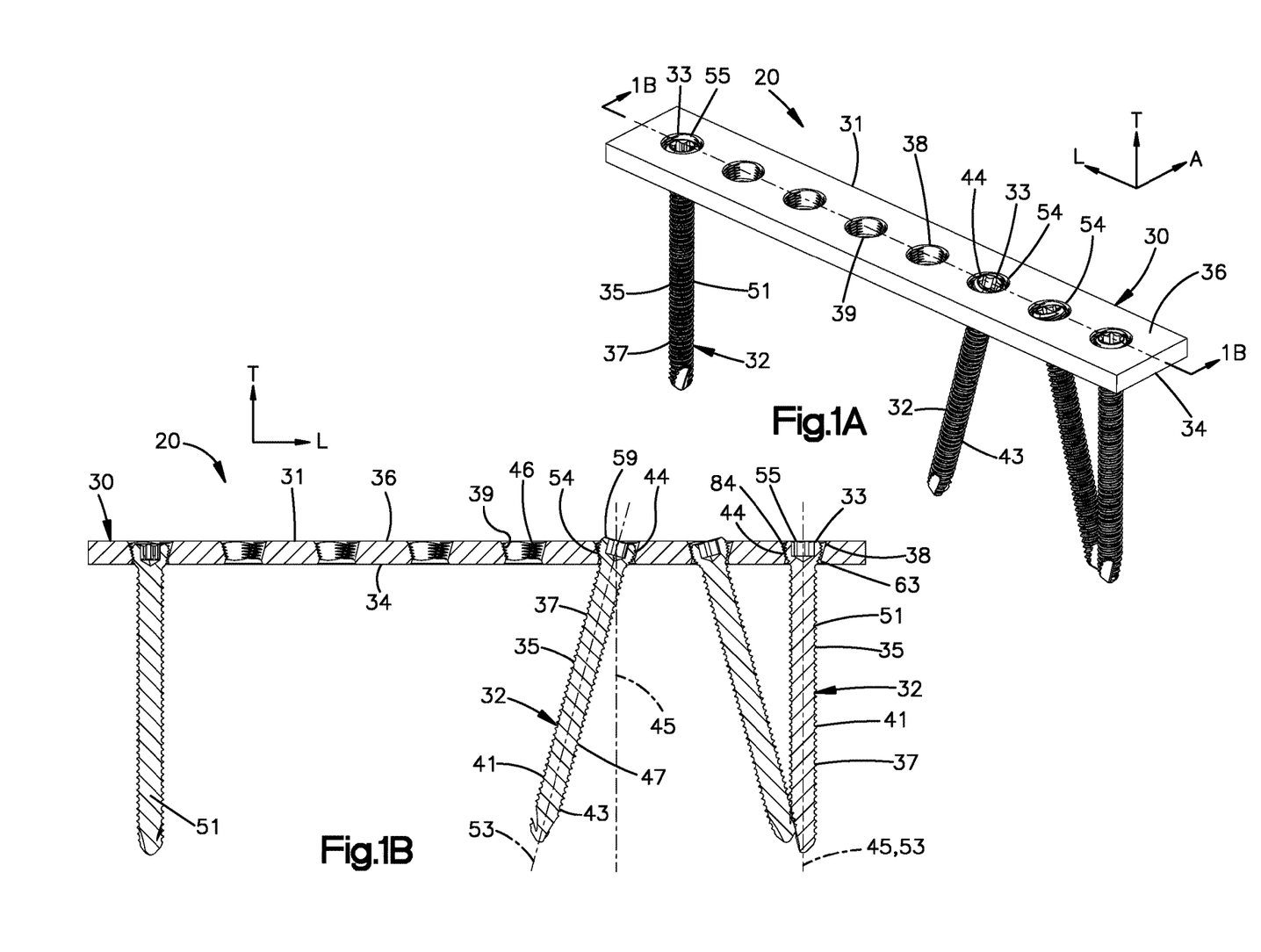
FIG. 1A is a schematic perspective view of a bone fixation system in accordance with one example of the present disclosure, including a bone plate and a plurality of bone fixation anchors.
FIG. 1B is a cross sectional elevation view of the bone plate illustrated in FIG. 1A, taken along line 1B-1B.
Figure 1C:
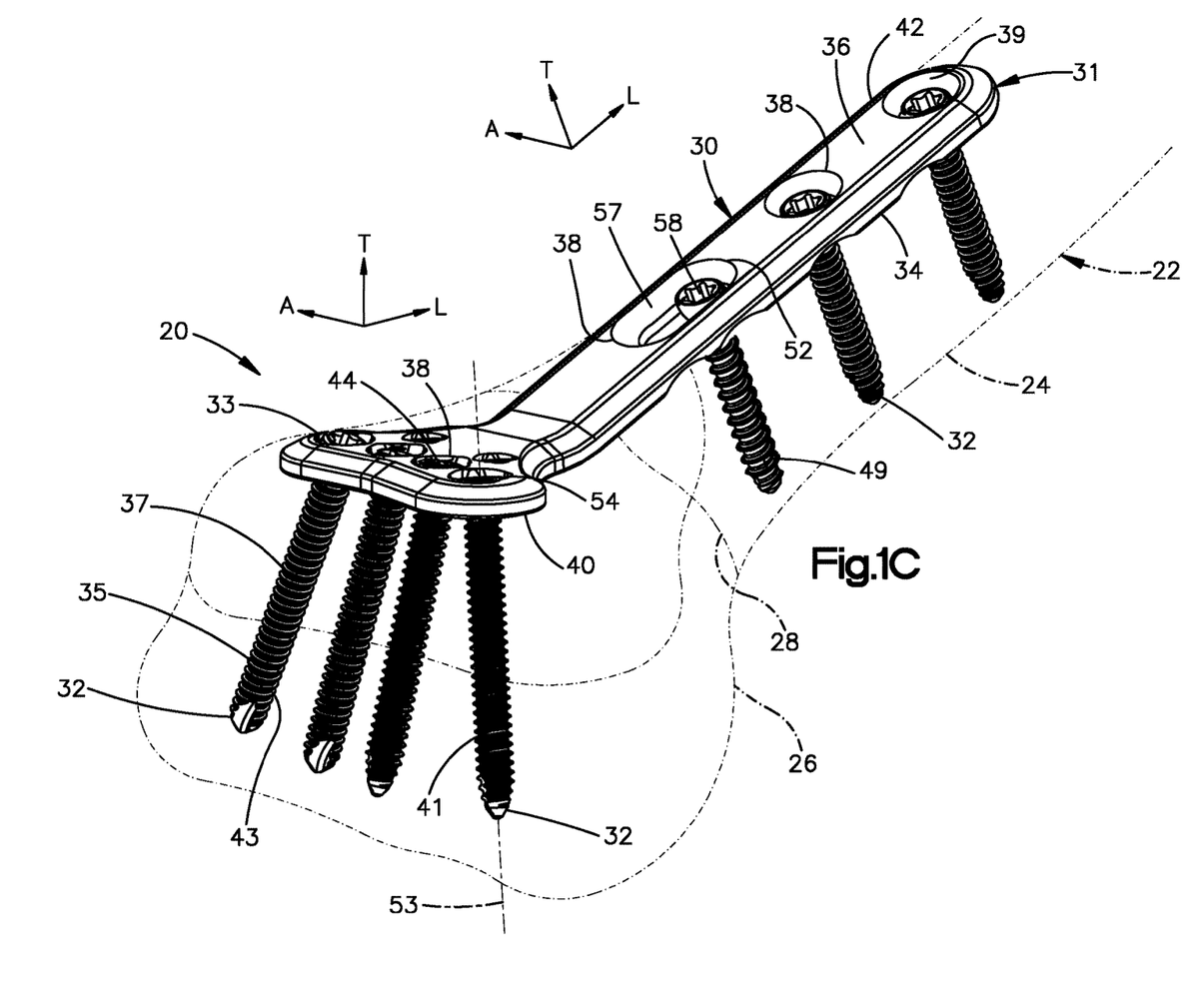
FIG. 1C is a perspective view of a bone plate constructed in accordance with one embodiment.
Figure 2A:
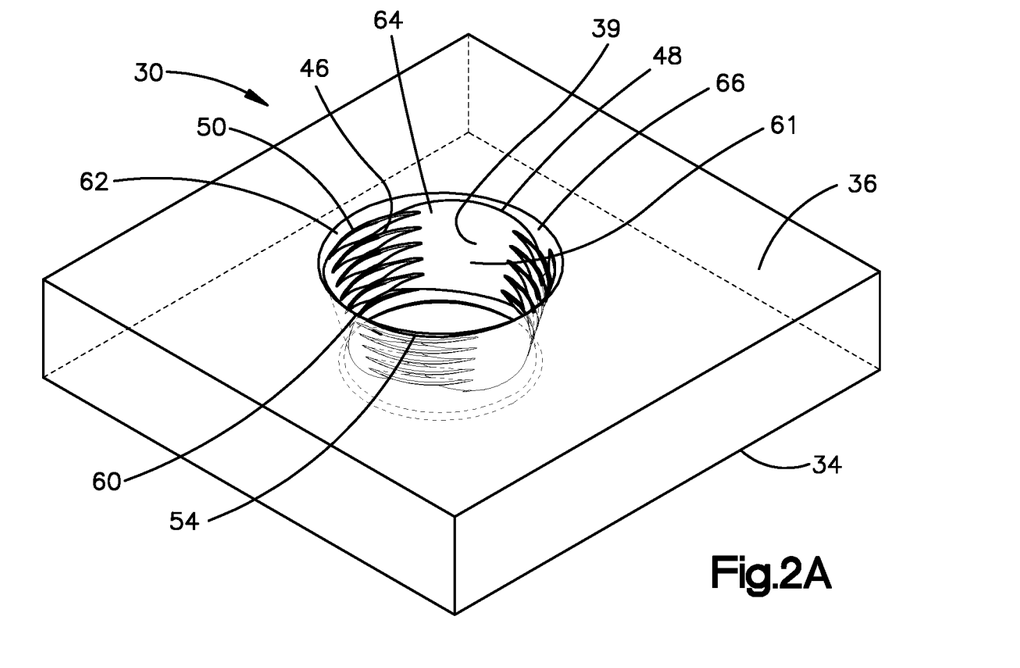
FIG. 2A is a top perspective view of a portion of the bone plate illustrated in FIG. 1A, showing a variable angle locking hole defined by an internal surface of the bone plate that includes a plurality of columns of thread segments.
Figure 2B:
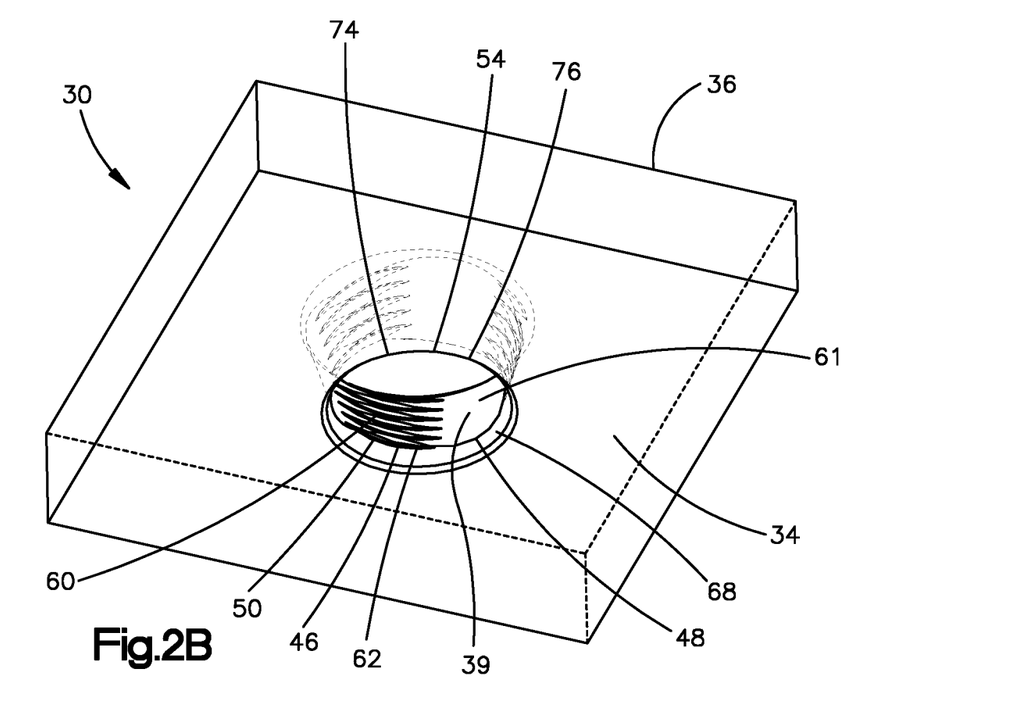
FIG. 2B is a bottom perspective view of the portion of the bone plate illustrated in FIG. 2A.
Figure 2C:
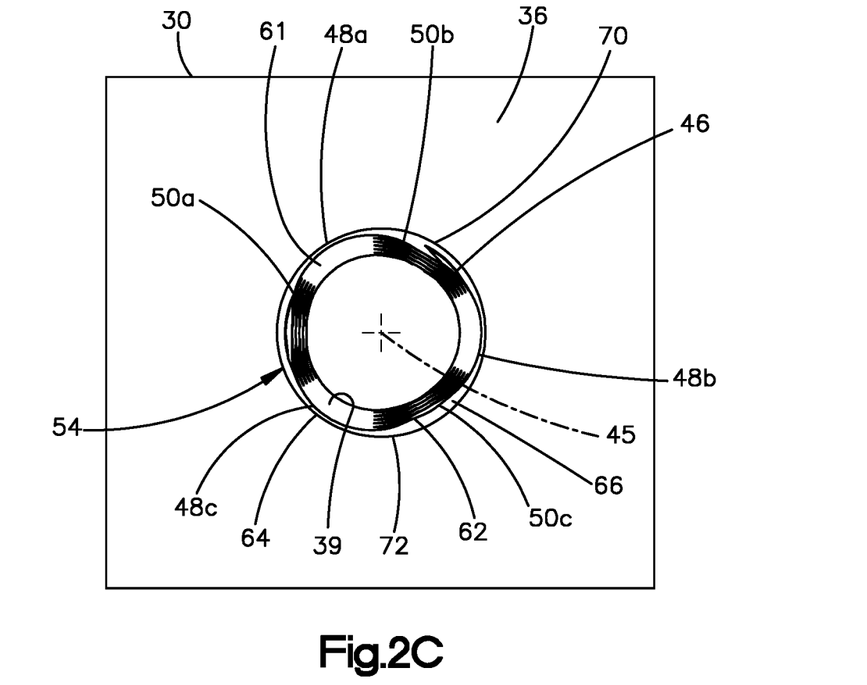
FIG. 2C is a top plan view of the portion of the bone plate illustrated in FIG. 2A.
Figure 2D:
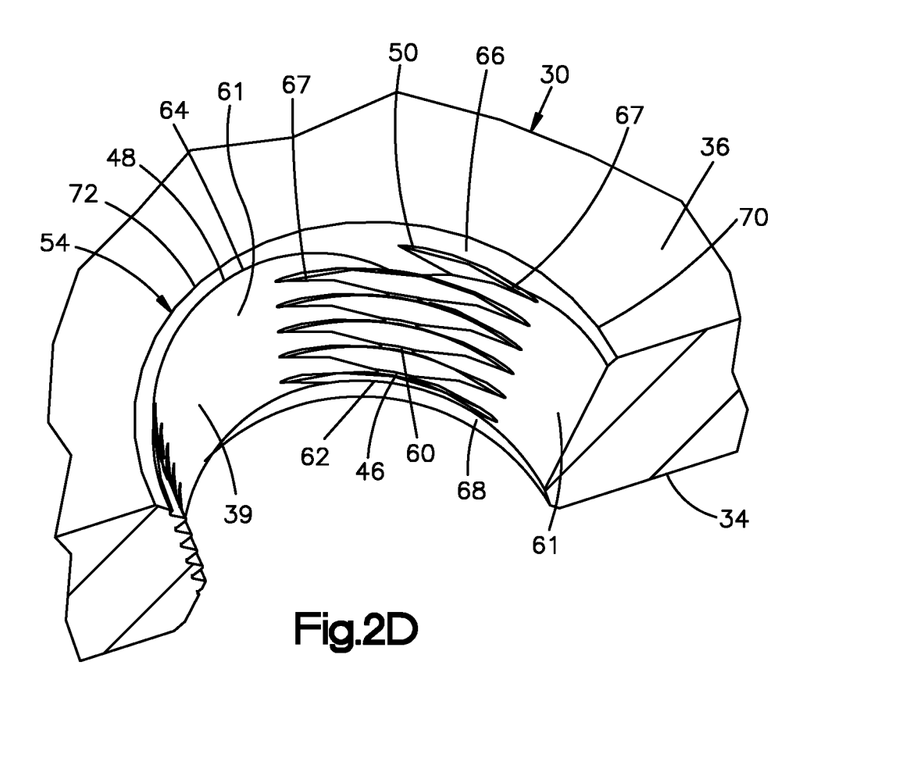
FIG. 2D is an enlarged sectional perspective view of a portion of the variable angle locking hole illustrated in FIG. 2A, showing columns of thread segments separated from each other by recesses.

Referring initially to FIGS. 1A-1C, a bone fixation system 20 is configured to be implanted onto bone 22 so as to stabilize a first bone segment 24 with respect to a second bone segment 26 that is separated from the first bone segment 24 by a defect 28. In one example, the first bone segment 24 can be defined by the diaphysis of the bone, while the second bone segment 26 can be defined by the epiphysis of the bone. It should be appreciated, however, that the first and second bone segments 24 and 26 can be defined by any region of the bone 22 as desired. Further, the bone 22 can be any bone in the human or animal anatomy suitable for bone plate fixation. Further still, while the bone 22 is illustrated having first and second bone segments 24 and 26, it is appreciated that the bone 22 can include any number of defects or bone fragments as desired that are configured for fixation using the bone fixation system 20. For instance, the diaphysis of the bone can include a plurality of bone fragments.

The bone fixation system 20 can include a bone plate 30 and a plurality of bone anchors 32 that are configured to fix the bone plate 30 to the underlying bone 22, and in particular to each of the first and second bone segments 24 and 26. The bone anchors 32 include a head 33 and a shaft 35 that extends out with respect to the head 33 in a distal direction along a central anchor axis 53. For instance, the shaft 35 can extend out directly from the head 33. Alternatively, the shaft 35 can extend out from a neck that extends between the head 33 and the shaft 35. The shaft 35 can extend directly from the head 33, or can extend from a neck that is disposed between the head 33 and the shaft 35. The shaft 35 can be threaded, such that the bone anchor 32 is configured as a bone screw 37 whose shaft 35 extends out relative to the head 33 along the central anchor axis 53, which can also be referred to as a central screw axis 53 when the bone anchor is configured as a bone screw. The threaded shaft 35 can be configured to threadedly purchase in the underlying bone 22. For instance, one or more up to all of the bone screws 37 can be configured as a cortical screw whose shaft 35 is threaded and designed and configured to threadedly mate to cortical bone. Alternatively or additionally, one or more of the bone screws 37 can be configured as a cancellous screw whose threaded shaft 35 is designed and configured to threadedly mate to cancellous bone. It is appreciated that the shafts of cancellous bone screws typically have threads with a greater pitch than the threads of the shafts of cortical bone screws. Further, the threads of cancellous bone screws typically extend out from the shaft of the bone screw a greater distance than the threads of cortical bone screws.

The bone plate 30 defines a bone plate body 31. The bone plate body 31, and thus the bone plate 30, defines a bone-facing inner surface 34 configured to face the underlying bone 22, and an outer surface 36 that is opposite the inner surface 34 along a transverse direction T. The bone plate 30 further defines a plurality of fixation holes 38 that extend through the bone plate body 31 from the inner surface 34 to the outer surface 36. In particular, the bone plate 30 can define a plurality of internal surfaces 39 that define the plurality of fixation holes 38, respectively. Each of the fixation holes 38 can extend through the bone plate body 31, and thus through the bone plate 30, along a respective central hole axis 45. The central hole axis 45 can be oriented along the transverse direction T. Thus, the central hole axis 45 can be oriented normal to each of the inner surface 34 and the outer surface 36. It should be appreciated, of course, that the central hole axis 45 can be oriented in any suitable direction as desired, including a direction oblique to the transverse direction T.

The fixation holes 38 are sized to receive the shaft 35 of a respective one of the bone screws 37. Thus, the bone screws 37 that extend through fixation holes 38 are permanent bone screws, meaning that they remain after completion of the surgical procedure. This is distinguished from temporary fixation holes that, for instance, can be configured to receive temporary fixation members, such as Kirschner wires that are removed prior to completion of the surgical procedure. In this regard, the fixation holes 38 can be referred to as permanent fixation holes. Accordingly, during operation, the shaft 35 of the bone screw 37 can be inserted through a respective one of the fixation holes 38 and into the underlying bone 22. The bone screw 37 can then be rotated so as to cause the threaded shaft 35 to be driven into the underlying bone 22 as the threaded shaft 35 threadedly purchases with the underlying bone. The threaded shaft 35 can be driven into the underlying bone 22 until the head 33 engages the bone plate 30, thereby securing the bone plate 30 to the underlying bone 22.

Figure 7A:
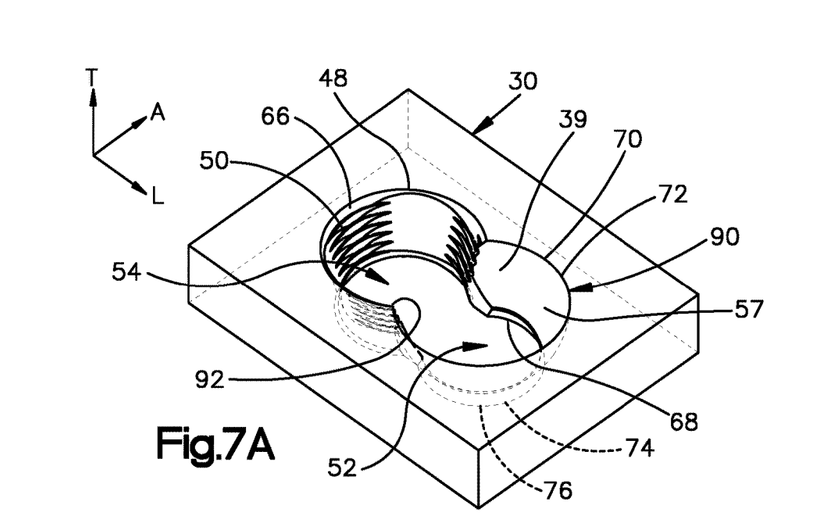
FIG. 7A is a perspective view of a bone plate having a combination hole that includes a variable angle locking hole portion and a compression hole that is open to the variable angle locking hole portion.
Figure 7B:
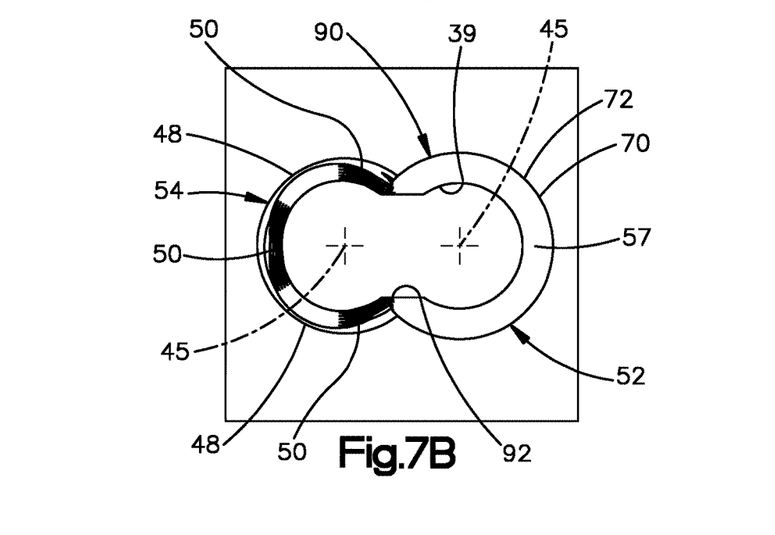
FIG. 7B is a top plan view of the bone plate illustrated in FIG. 7A.
Figure 7C:
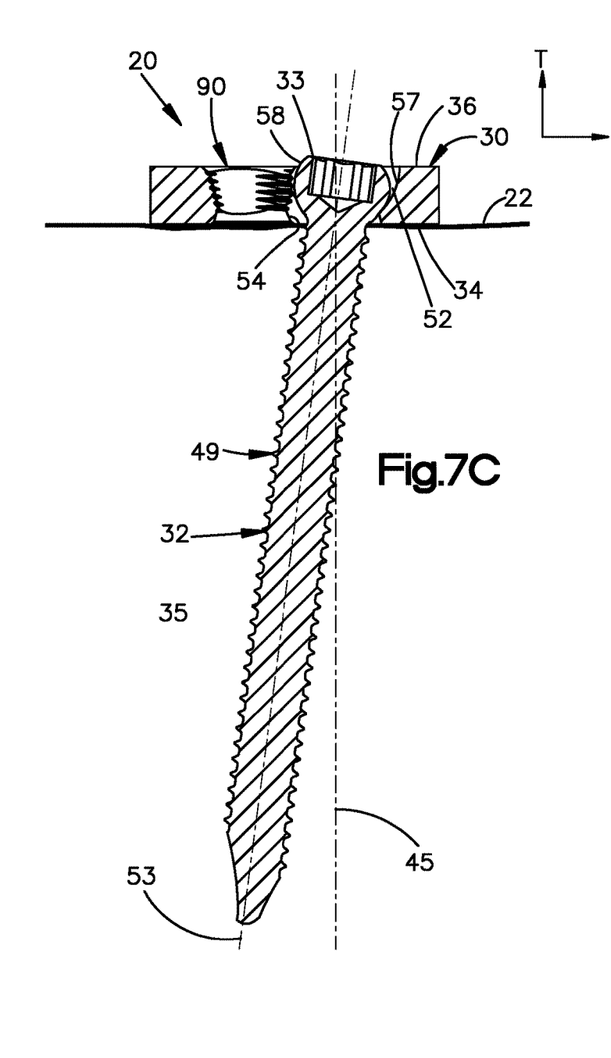
FIG. 7C is a cross-sectional view of the bone plate illustrated in FIG. 7A, showing a variable angle compression bone screw inserted into the compression hole of the combination hole and threadedly purchased in an underlying bone.

Certain ones of the fixation holes 38 can be unthreaded compression holes 52, while certain others of the fixation holes 38 can be threaded locking holes 44 and some holes can be a combination thereof, where a threaded locking hole 44 and an unthreaded compression hole 52 intersect each other to define a combination hole 90 (see FIGS. 7A-7C). The bone plate 30 defines an internal compression surface 57 that can extend between the outer surface 36 and the inner surface 34 so as to at least partially define the compression hole 52. The internal surface 39 can extend from the outer surface 36 to the inner surface 34, and can be threaded so as to define the locking hole 44.

Thus, one or more of the bone screws 37 can be configured as a compression screw 49 whose head 33 defines a compression head 58 that is configured to bear against the bone plate 30 in the compression hole 52 so as to apply a compressive force against the bone plate 30 toward the underlying bone 22. In particular, during operation, the shaft 35 of the compression screw 49 can be threaded and inserted through the compression hole 52 and driven into the underlying bone 22 as described above. In particular, rotation of the bone screw 37 causes the shaft 35 to advance distally into the underlying bone, which thereby causes the compression head 58 to compress against the internal compression surface 57. As a result, the compression head 58 causes the bone plate 30 to apply a compressive force against the underlying bone. At least a portion of the internal compression surface 57 is typically spherical or tapered as it extends from the outer surface 36 toward the inner surface 34 so as to prevent the compression head 58 from passing completely through the compression hole 52. The compression head 58 typically has an unthreaded external surface. Similarly, at least a portion up to an entirety of the internal compression surface 57 that abuts the unthreaded external surface of the compression head 58 is typically unthreaded. Thus, it is common to drive compression screws 49 into the unthreaded compression holes 52. However, as is described in more detail below with respect to FIGS. 7A-7C, the compression screws 49 can also be driven into the combination hole 90.

Alternatively, one or more up to all of the bone screws 37 can be configured as locking screws 41 that are configured to threadedly purchase with the bone plate 30 inside the threaded locking holes 44. In particular, the head 33 of the locking screws 41 be a locking head 55 that carries at least one external thread 63. The thread 63 can be a helical thread. The shaft 35 of the locking screw 41 can similarly be threaded. During operation, the shaft 35 of the locking screw 41 can be inserted through the fixation hole 38 and driven into the underlying bone 22 as described above. In particular, rotation of the screw 37 causes the shaft 35 to advance distally into the underlying bone 22, which causes the locking head 55 to advance toward the threaded locking hole 44 of the bone plate. As the screw 37 is continuously rotated, the locking head 55 can threadedly mate with the threaded internal surface 39 of the bone plate that defines the threaded locking hole 44. In particular, the at least one external thread 63 of the locking screw 41 can threadedly mate with a corresponding at least one thread 46 that extends out from the internal surface 39. As a result, the locking screw 41 can secure the bone plate 30 to the underlying bone 22 without applying a compressive force onto the bone plate 30 against the underlying bone 22. The bone plate 30 can be spaced from the underlying bone 22 when locked to the locking head 55. Alternatively, the bone plate 30 can abut the underlying bone 22 when locked to the locking head 55. At least a portion of the internal surface 39 can be tapered as it extends from the outer surface 36 toward the inner surface 34. Thus, the internal surface 39 is configured to prevent the locking head 55 from passing completely through the threaded locking hole 44.

One or more of the locking screws 41 can be configured as a standard-type locking screw 51. The locking head 55 of a standard-type locking screw 51 can be referred to as a standard-type locking head 55 having an external thread 84. The external thread 84 is configured to threadedly purchase to the bone plate 30 in the locking hole 44 only when the standard-type locking screw 51 is at predetermined orientation with respect to the central hole axis 45. For instance, the predetermined orientation can be the nominal orientation whereby the central screw axis 53 is coincident with the central hole axis 45. Further, the external thread 84 can be misaligned with the internal surface 39 of the locking hole 44 with respect to threaded mating when the central screw axis 53 is not in the predetermined orientation with the central hole axis 45.

Further, one more of the locking screws 41 can be configured as a variable angle (VA) locking bone screw 43. The locking head 55 of the VA locking bone screw 43 can be configured as a VA threaded head 59, and the shaft 35 of the VA locking bone screw 43 can be referred to as a VA threaded shaft 47. As will be appreciated from the description below, VA locking bone screw 43 can include a plurality of portions that are separate from each other and attached to each other. For instance, a first portion of the VA locking bone screw 43 can include the locking head, and a second portion of the VA locking bone screw 43 can include at least a portion up to an entirety of the VA threaded shaft 47. As will be appreciated from the description below, the first portion can have a material hardness that is greater than that of the second portion.

One or more of the threaded locking holes 44 can be configured as variable angle (VA) locking holes 54 that is configured to receive a respective one or more of the VA locking bone screws 43. In particular, the internal surface 39 of the bone plate 30 is configured to threadedly mate with the VA threaded head 59 in the VA locking holes 54 when the central screw axis 53 of the VA bone screw 43 is oriented at any one of a plurality of angles within a range of angles with respect to the central hole axis 45 at which the VA threaded head 59 is configured to threadedly mate with the bone plate 30 in the VA locking hole 54. The bone plate 30 can be referred to as a locking compression plate, as its fixation holes are configured to engage compression screws and locking screws, respectively.

As illustrated in FIG. 1C, the bone plate 30 can be configured to be secured to the underlying bone 22 to promote healing of the defect 28. In one example, the bone plate body 31, and thus the bone plate 30, can include a first plate portion that can define a plate head portion 40 that is configured to overlie the second bone segment 26, and a second plate portion that can be referred to as a plate shaft portion 42 that is configured to overlie the first bone segment 24. Each of the plate head portion 40 and the plate shaft portion 42 can include at least one up to a plurality of bone fixation holes 38. Thus, bone anchors 32 that extend through respective fixation holes 38 of the plate head portion 40 can be driven into the epiphysis region of the underlying bone, and bone anchors 32 that extend through respective fixation holes 38 of the plate shaft portion 42 can be driven into the diaphysis region of the underlying bone. The epiphysis region can, for instance, be defined by the distal region of the radius bone. Any one or more up to all of the fixation holes 38 of the bone plate 30 can be compression holes, locking holes, VA locking holes or a combination thereof (also referred to as the "combination holes").

In one example, one or more up to all of the fixation holes 38 in the plate head portion 40 can be configured as VA locking holes 54. Further, in one example, one or more up to all of the fixation holes 38 in the plate shaft portion 42 are compression holes 52 configured to receive cortical bone screws. Further, at least one or more up to all of the compression holes can be configured as slots that are elongate along a central longitudinal axis of the bone plate 30 to allow for positional flexibility of the bone screw 37 received therein. Alternatively or additionally, at least one or more up to all of the compression holes can have a circular cross-section so as to locate the position of the bone screw 37 received therein. While the bone plate 30 has been described in accordance with one specific example, it should be appreciated that the bone plate 30 can be configured in any suitable manner as desired. Further, bone plates 30 constructed in accordance with any of the examples described herein can be configured to attach to any region or region or regions of any suitable bone in the human or animal anatomy suitable for bone plate fixation.

The VA locking hole 54 will now be described in more detail with respect to FIGS. 2A-2D. As described above, the internal surface 39 of the bone plate 30 can be threaded, and can extend from the outer surface 36 to the inner surface 34 so as to define the VA locking hole 54 that extends from the outer surface 36 to the inner surface 34. In particular, the VA locking hole 54 extends along the central hole axis 45. The central hole axis 45 can be oriented along the transverse direction T. Thus, the central hole axis 45 can be oriented normal to either or each of the inner surface 34 and the outer surface 36. It should be appreciated, of course, that the central hole axis 45 can be oriented in any suitable direction as desired, including a direction oblique to the transverse direction T.

As described above with respect to the threaded locking hole 44 of the bone plate 30, the internal surface 39 of the VA locking hole 54 can be threaded. For instance, the internal surface 39, and thus the bone plate 30, can define a plurality of threaded regions 62 that each carries at least one thread 46. Alternatively, the bone plate 30 can include a threaded insert in the VA locking hole 54, whereby the threaded insert carries the at least one thread 46. The internal surface 39, and thus the bone plate 30, can further define a plurality of recessed regions 64 that are disposed circumferentially between respective adjacent ones of the threaded regions 62. Thus, the threaded regions 62 and the recessed regions 64 can be alternatingly arranged with each other circumferentially about the central hole axis 45. The threaded regions 62 and the recessed regions 64 are configured such that the VA locking screws 43 are configured to threadedly purchase with the internal surface 39 at the threaded regions 62 without threadedly purchasing with the internal surface 39 at the at least one recessed regions 64.

In one example, the at least one thread 46 projects out from the internal surface 39 at the threaded regions 62 into the VA locking hole 54 generally toward the central hole axis 45. The at least one thread 46 can be monolithic with the internal surface 39. The at least one thread 46 can extend along a thread path. The thread path can be a helical thread path. In one example, the at least one thread 46 can be a single lead thread, a double lead thread, or any suitably constructed thread as desired. The internal surface 39 can further define a recess 48 at each of the recessed regions 64. The recesses 48 can circumferentially interrupt the at least one thread 46 so as to define a plurality of thread segments 60. Axially aligned ones of the thread segments can combine to define a plurality of threaded columns 50. Thus, it can be said that the threaded columns 50 are defined by thread segments 60. Because the at least one thread 46 can extend along a helical thread path, the threaded columns 50 can have different numbers of thread segments 60. The recesses 48 and the columns 50 can be alternatingly arranged with each other circumferentially about the central hole axis 45. The at least one recess 48 is offset with respect to the columns 50 of thread segments 60 in a radially outward direction. The internal surface 39 can be said to define a recessed surface 61 at the recesses 48.

The axial direction is defined as a direction between the outer surface 36 and the inner surface 34 of the bone plate 30. Thus, the directional term "axially inward" and derivatives thereof as used herein refers to a direction from the outer surface 36 toward the inner surface 34. Conversely, the terms "axially outward" and derivatives thereof as used herein refers to a direction from the inner surface 34 toward the outer surface 36. The axially inward and axially outward directions can be oriented along the central hole axis 45. Alternatively, the axially inward and axially outward directions can be oriented along a direction oblique to the central hole axis 45, for instance when used with reference to the internal surface 39.

The recesses 48 can have a radial depth sufficient such that the recessed surface 61 is recessed with respect to the internal surface 39 at the columns 50 along the radially outward direction. That is, the recessed surface 61 can define a radial distance from the central hole axis 45 that is greater than the radial distance from the central hole axis 45 to the major diameter of the at least one thread 46 of the columns 50. Therefore, during operation, a threaded bone screw head 33 that threadedly purchases with the internal surface 39 at the columns 50 of thread segments 60 are spaced radially inward from the internal surface 39 at the recess 48. The recessed surfaces 61 can be devoid of the thread 46. For instance, the recessed surfaces 61 can be unthreaded and smooth.

The thread segments 60 of each of the columns 50 are spaced from each other in the axial direction so as to define interstices that receive corresponding external threads of a locking screw head 33. The axially aligned thread segments 60 of at least a portion of the axial lengths of the columns 50 can each have a common circumferential length. In one example, all thread segments 60 of each of the columns 50 can have the same circumferential length. Accordingly, lines along circumferentially ends of the columns 50 can lie in respective planes that also include the central hole axis 45.

Thus, the thread segments 60 of each of the columns 50 can be circumferentially offset from the thread segments 60 of the other ones of the columns 50. Further, adjacent ones of the circumferentially spaced thread segments 60 can be separated by a respective common one of the recesses 48. Thus the thread segments 60 of each column 50 can be aligned with the thread segments 60 of one or both adjacent column 50 along the thread path. Because the thread path can be helical, the thread segments 60 can be aligned with the thread segments 60 of an adjacent one of the columns 50 along a helical path. In one example, each of the thread segments 60 of a respective one of the columns 50 is aligned along the thread path with 1) one the thread segments 60 a first adjacent column 50, and 2) one the thread segments 60 of a second adjacent column 50. Thus, the respective one of the columns 50 is disposed circumferentially between the first adjacent column 50 and the second adjacent column 50. Further, the thread segments 60 of the respective one of the columns 50 is disposed between the first one of the thread segments 60 and the second one of the thread segments 60 with respect to the axial direction.

In one example, the bone plate 30 can include three recesses 48. The recesses 48 are circumferentially spaced apart from each other. However, it is appreciated that the bone plate 30 can include any number of recesses 48, greater than one, as desired, so as to define the variable angle locking hole 54 of the type described herein. Further, the respective radial distance of the recessed surfaces 61 of each of the recesses 48 can be the same as each other. In this regard, each of the recesses 48 can be substantially (within manufacturing tolerance) identical to each other. Further, the recesses 48 can be circumferentially equidistantly spaced from each other about the central hole axis 45. Alternatively, the recesses 48 can be circumferentially spaced from each other at a variable distance about the central hole axis 45.

Each of the recesses 48 can define an adjacent pair of the columns 50. Further, the bone plate 30 can define an equal number of recesses 48 and columns 50. Thus, in one example, the bone plate 30 can include three columns 50a, 50b, and 50c of thread segments 60 in one example. The columns 50 are circumferentially spaced apart from each other. However, it is appreciated that the bone plate 30 can include any number of columns 50, greater than one, as desired, so as to define the variable angle locking hole 54 of the type described herein. Each adjacent pair of columns 50 can be separated from each other by a respective recess 48. The columns 50 can be substantially (within manufacturing tolerance) identical to each other. Further, the columns 50 can be circumferentially equidistantly spaced from each other about the central hole axis 45. Alternatively, the columns 50 can be circumferentially spaced from each other at a variable distance about the central hole axis 45.

Figure 3:
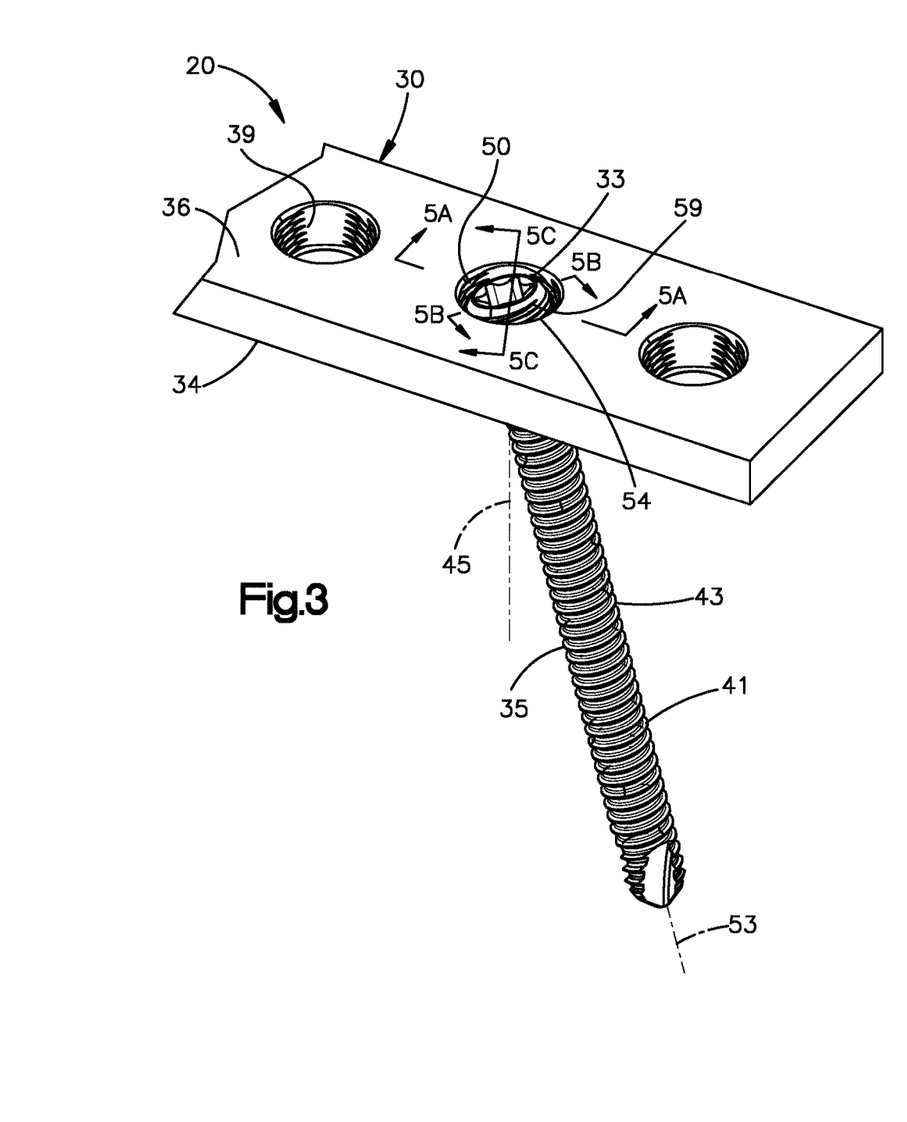
FIG. 3 is a perspective view of a variable angle locking bone screw mated in the variable angle locking hole illustrated in FIG. 2A at an oblique orientation.
Figure 4:
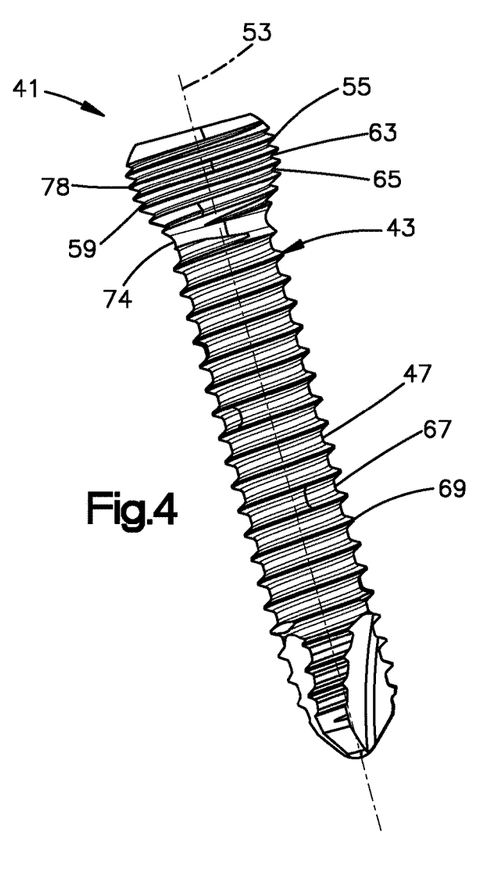
FIG. 4 is a perspective view of the variable angle locking bone screw illustrated in FIG. 3.
Figure 5A:
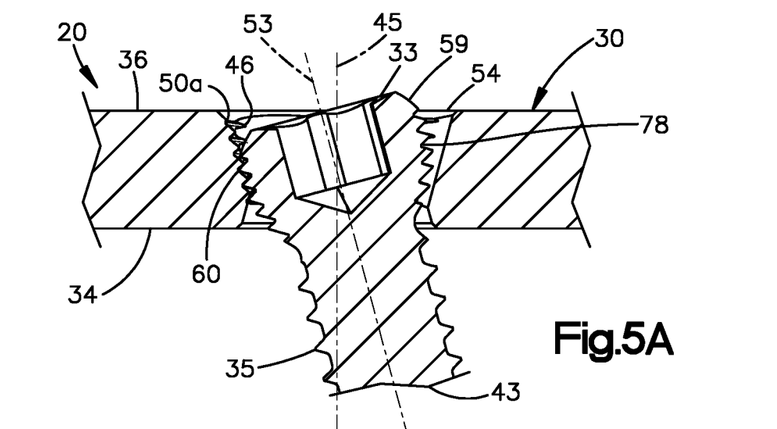
FIG. 5A is a cross-sectional view of the variable angle locking hole illustrated in FIG. 3 taken along line 5A-5A, showing the head of the variable angle locking bone screw threadedly purchased with a first one of the columns of thread segments.
Figure 5B:
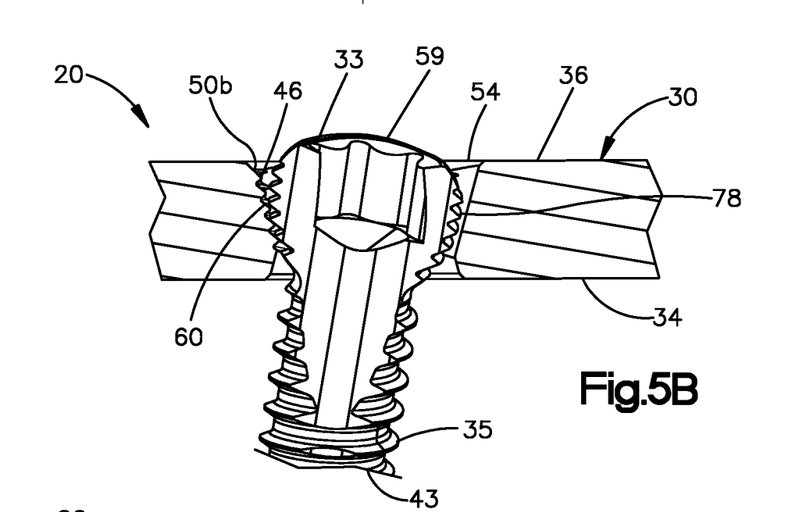
FIG. 5B is a cross-sectional view of the variable angle locking hole illustrated in FIG. 3 taken along line 5B-5B, showing the head of the variable angle locking bone screw threadedly purchased with a second one of the columns of thread segments.
Figure 5C:
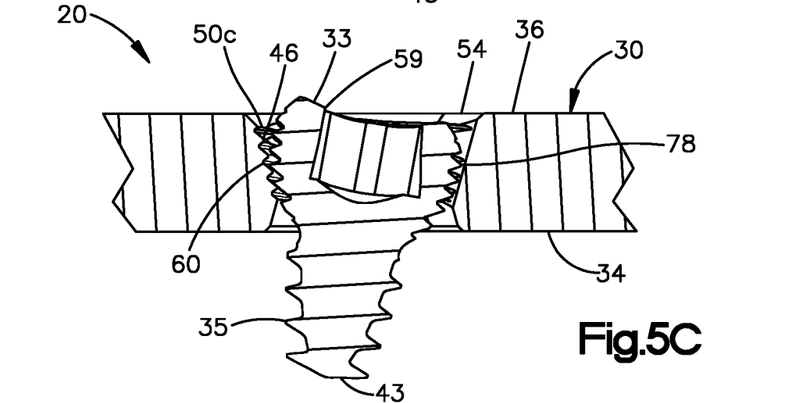
FIG. 5C is a cross-sectional view of the variable angle locking hole illustrated in FIG. 3 taken along line 5C-5C, showing the head of the variable angle locking bone screw threadedly purchased with a third one of the columns of thread segments

With additional reference to FIGS. 3-4, the columns 50 allows for the bone plate 30 to mate with the VA threaded head 59 of the VA locking screw 43 in the VA locking hole 54 at an angle within a range of angles, such that the VA threaded head 59 threadedly purchases with a plurality of the columns 50 of thread segments 60 simultaneously. The angle and the range of angles are defined by the central screw axis 53 and the central hole axis 45. In particular, at least one external thread 78 of the VA threaded head 59 can threadedly mate with the at least one thread 46 of the bone plate 30, and in particular with respective ones of the thread segments 60 at the angle. In one example, the threaded head can threadedly purchase with all of the columns 50 of thread segments 60 simultaneously at the angle. The angle can be one of any angle within the range of angles when the central screw axis 53 is oblique to the central hole axis 45, and at which the VA threaded head 59 can mate with the bone plate 30 in the VA locking hole 54.

Referring again to FIGS. 2A-2D, while the threaded regions 62 include respective columns 50 of threaded segments 60, it should be appreciated that the internal surface 39 need not be threaded along its entirety at locations axially aligned with the columns 50. For instance, the internal surface 39 can include a tapered lead-in surface 66 at the axially outer end of the VA locking hole 54. Thus, the lead-in surface 66 can extend from the outer surface of the bone plate 30 to the columns 50. Further, the internal surface 39 can include a tapered undercut surface 68 at the axially inner end of the VA locking hole 54. Thus, the tapered undercut surface 68 can extend from the inner surface of the bone plate 30 to the columns 50. Either or both of the lead-in surface 66 and the undercut surface 68 can be unthreaded in one example.

It should be appreciated that the columns 50 can extend from the lead-in surface 66 to the undercut surface 68. Further, the columns 50 can taper radially inward toward the central hole axis 45 as they extend axially inward. In one example, the columns 50 can extend linearly along the axial direction from the lead-in surface 66 to the undercut surface 68. Further, the VA locking hole 54 can be constructed such that no portion of the internal surface 39 extends radially inward of the columns 50. Therefore, the VA locking screw 43 described herein can threadedly purchase within the columns 50 without contacting any other surface except for the columns 50 and the undercut surface 68.

Referring now to FIGS. 3-4 in particular, the VA locking holes 54 can be configured to threadedly receive the VA locking screw 43. When the locking screw 41 is configured as a VA locking screw 43, the locking head 55 can be configured as a VA locking head 59. Further, when the locking screw 41 is configured as the VA locking screw 43, the at least one external thread 63 of the VA locking head 59 can be configured as at least one external VA thread 78. The VA threaded shaft 47 can define an outer surface 67 and at least one thread 69 that projects out from the outer surface 67. The at least one thread 69 can be a helical thread. The VA locking screw 43 is configured to threadedly mate with the bone plate 30 in the VA locking hole 54 at different orientations of the VA locking screw 43 with respect to the central hole axis 45.

The VA threaded head 59 can be constructed in accordance with any suitable example, for instance as described in U.S. Pat. No. 8,574,268, the disclosure of which is hereby incorporated by reference as if set forth in its entirety herein. Thus, the VA threaded head 59 can define an outer surface 65, and the at least one external thread 78 can extend out from the outer surface 65. The outer surface 65 can be curved. For instance, the outer surface 65 can be convex. In particular, the outer surface 65 can be spherical. The at least one external thread 78 can define a thread peak and a thread trough (or crest and root in thread terminology, respectively). Each of the thread peak and the thread trough can like on respective first and second curved or spherical paths. Thus, each of the thread peak and the thread trough can be defined by respective radii, wherein a first radius of the thread peak is greater than a second radius of the thread trough. Further, the center of the first and second spherical paths can coincide with the center of the spherical outer surface 65. In one example, the center of the outer surface 65 and the center of the first and second spherical paths can define a geometrical center of the VA threaded head 59.

It should be appreciated that the outer surface 65 can be geometrically defined in any suitable manner as desired to achieve variable angle locking as described herein. For instance, the outer surface 65 can be conically shaped in one example. Thus, the thread peaks and thread troughs can similarly be conically shaped. Further, the external thread 78 of the VA threaded head 59 of the VA locking screw 43 can be circumferentially continuous about the central screw axis 53. It should be appreciated, however, that the VA threaded head 59 can be alternatively constructed in any manner desired so as to threadedly mate with the at least one thread 46 in the manner described herein.

Otherwise stated, and referring to FIGS. 3 and 5A-5C, the VA locking screw 43 is configured to be inserted into the VA locking hole 54 such that the central screw axis 53 is at one of a plurality of angles with respect to the central hole axis 45 within a range of angles at which the VA threaded head 59 is configured to threadedly mate with the at least one thread 46 in the VA locking hole 54. For instance, the VA locking screw 43 is configured to be inserted into the VA locking hole 54 such that the central screw axis 53 is at one of a plurality of angles within a range of angles defined by the central screw axis 53 and the central hole axis 45 at which the VA threaded head 59 is configured to threadedly mate with each of the columns 50a, 50b, and 50c. The range of angles can be disposed within a cone that is centered about the central hole axis 45. In one example, the range of angles can be disposed within a cone of up to thirty degrees. The range of angles can be measured as 15 degrees with respect to the central hole axis 45. The central hole axis 45 can define the center of the cone. Thus, the VA threaded head 59 of the VA locking screw 43 can mate with the bone plate 30 in the manner described herein both when central screw axis 53 of the VA locking screw 43 is coincident with the central hole axis 45 and when the central screw axis 53 of the VA locking screw 43 is at any other angle with respect to the central hole axis 45 within the range of angles.

Thus, it can be said that the at least one thread 46 of the bone plate is configured to threadedly mate with the VA threaded head 59 while the VA locking screw 43 is inserted into the VA locking hole 54 such that the central screw axis 53 is oriented at a first angle with respect to the central hole axis 45, and the at least one thread 46 is further configured to threadedly mate with the VA threaded head 59 when the VA locking screw 43 is inserted into the VA locking hole 54 such that the central screw axis 53 is oriented at a second angle with respect to the central hole axis 45 that is different than the first angle. At least one or both of the first and second angles can be non-zero angles. Alternatively, the central screw axis 53 can be coincident with the central hole axis 45 in one of the orientations in the range of orientations. The at least one thread 46 and the threads of the VA threaded head 59 are defined prior to insertion of the VA locking screw 43 into the VA locking hole 54. That is, the internal surface 39 is not designed or configured to cut or form threads into the VA threaded head 59. Similarly, the VA threaded head 59 is not designed or configured to cut or form threads into the internal surface 39. It is recognized, however, that after locking of the VA locking screw 43 in the VA locking hole 54, the respective roots of the thread segments 60 that are mated with the VA threaded head 59 can undergo a small amount of elastic and/or plastic deformation.

The VA locking hole 54 is configured to receive the VA locking screw 43 such that more than one of the columns up to all of the columns 50 threadedly purchase with the externally threaded VA threaded head 59 of the VA locking screw 43 when the central screw axis 53 and the central hole axis 45 define any angle within the range of angles that are disposed within the range of angles. In particular, two or more of the columns 50 up to all of the columns 50a-50c can threadedly purchase with the externally threaded VA threaded head 59 of the VA locking screw 43 when the VA threaded head 59 is mated with the bone plate 30 in the VA locking hole 54 while the central screw axis 53 is within the range of angles with respect to the central hole axis 45.

Figure 6A:
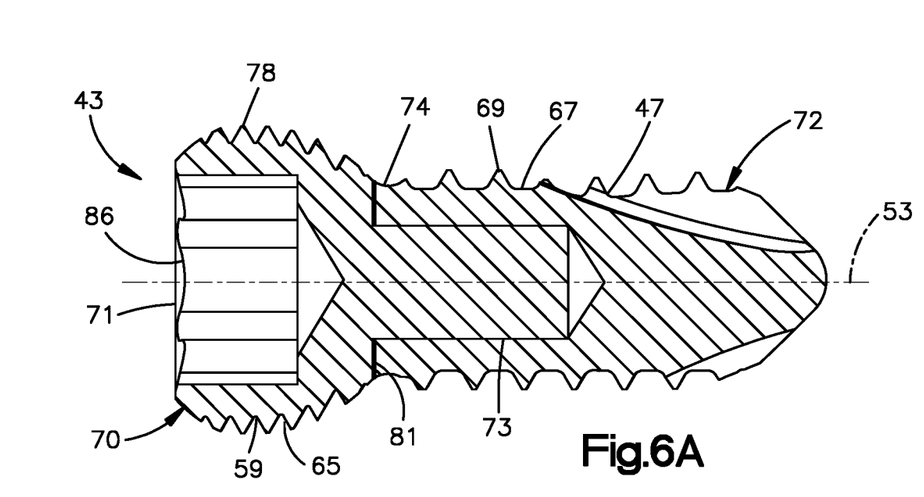
FIG. 6A is sectional side elevation view of the variable angle locking bone screw illustrated in FIG. 4, showing a first portion and a second portion attached to the first portion.
Figure 6B:
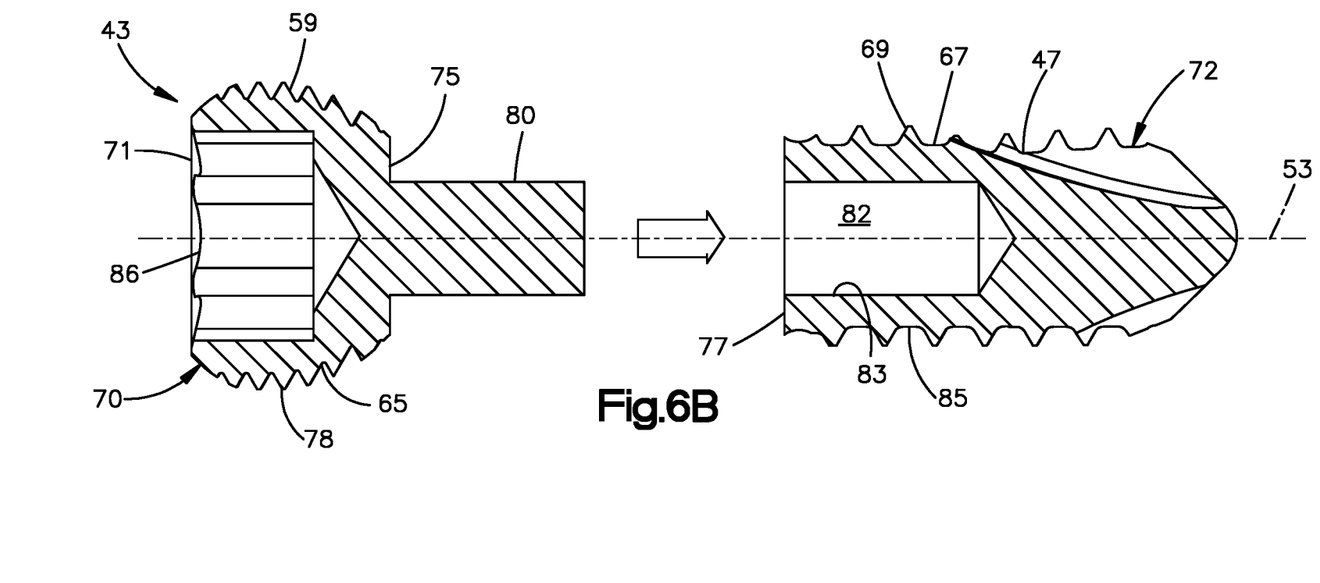
FIG. 6B is an exploded sectional side elevation view of the variable angle locking bone screw illustrated in FIG. 6A.

Referring now to FIGS. 6A-6B, and as described above, the VA locking screw 43 can be configured as a two piece screw having a first portion 70 and a second portion 72 that is separate from the first portion 70. The first portion 70 can include at least a portion of the VA threaded head 59, and the second portion 72 can include at least a portion of the VA threaded shaft 47. The second portion 72 can also include the distal tip of the VA locking screw 43. The distal tip can be self-tapping in some examples. In one example, the first portion 70 can include an entirety of the VA threaded head 59. Thus, the first portion 70 can include an entirety of the at least one external VA thread 78. Alternatively, the first portion 70 can include a portion less than an entirety of the at least one external VA thread 78. Further, the second portion 72 can include an entirety of the VA threaded shaft 47. Thus, the second portion 72 can include an entirety of the at least one thread 69. Alternatively, the second portion 72 can include a portion less than an entirety of the at least one thread 69.

The first and second portions 70 and 72 can further include respective first and second portions of a neck 74 that extends from the threaded VA threaded shaft 47 to the VA threaded head 59. The neck 74 can be unthreaded in one example, and can flare radially outward from the VA threaded shaft 47 to the VA threaded head 59. In this regard, it should be appreciated that the VA threaded head 59 can define a greater diameter than the VA threaded shaft 47. In one example, each of the first and second portions 70 and 72 can be a one-piece monolithic body.

Because the first and second portions 70 and 72 are separate from each other, at least a portion of the first portion 70 can be fabricated having a material hardness greater than the second portion 72. That is, either or both of the at least the outer surface 65 and the at least one external thread 78 of the VA threaded head 59 can have a material hardness greater than the material hardness of either or both of the outer surface 67 and at least one thread 69 of the VA threaded shaft 47. Otherwise stated, either or both of the outer surface 65 and the at least one external thread 78 can have a first hardness, and either or both of the outer surface 67 and the at least one thread 69 can have a second hardness that is less than the first hardness. In one example, the first portion 70 and the second portion 72 can be made from the same material, but the first portion 70 can be treated with a hardening process. For instance, the first portion 70 can be subjected to a hardening process to harden at least a portion of either or both of the outer surface 65 of the VA threaded head 59 and the at least one external thread 78 that is defined by the first portion 70. The hardening process can include a nitrogen diffusion or nitriding process, an oxygen diffusion hardening, or any suitable alternative hardening process. As will be described in more detail below, the hardening process renders the at least one external thread 78 of the VA threaded head 59 harder than the internal surface 39 of the bone plate 30. Thus, the at least one external thread 78 of the VA threaded head 59 can have a cantilever strength greater than that of the at least one thread 46 of the bone plate 30. Further, the outer surface 67 of the VA threaded shaft 47 can be non-hardened. Alternatively, in some examples, the VA locking bone screw 43 can be a single monolithic structure that includes the VA threaded head 59 and the VA threaded shaft 47. In this example, at least a portion up to an entirety of the VA locking bone screw 43 can be hardened using an oxygen diffusion hardening process. Thus, the VA locking bone screw 43, including the VA threaded head 59, can be oxygen diffusion hardened. As described above, a masking process can be used to selectively harden the VA threaded head 59 in an oxygen diffusion hardening process, without hardening the VA threaded shaft 47 if desired.

In one example, the second portion 72 can be a commercially pure titanium or titanium alloy, and the second portion can be a hardened commercially pure titanium or hardened titanium alloy. In one particular example, the second portion can be non-hardened Ti-6Al-7Nb (TAN), and the first portion 70 can be a hardened TAN. It should be appreciated, of course, that the first and second portions 70 and 72 can each be made of any suitable alternative biocompatible material as desired, such as other titanium alloys, commercially pure titanium or stainless steel. In this regard, the first portion 70 can be a hardened commercially pure titanium. The second portion 72 can be a non-hardened commercially pure titanium. Alternatively, the first and second portions 70 and 72 can be made from Ti-6Al-4V (TAV). Thus, the first portion 70 can be a hardened TAV, and the second portion 72 can be a non-hardened TAV. Alternatively or additionally still, the first and second portions 70 and 72 can be made of cobalt-chrome-molybdenum (CCM). Thus, the first portion 70 can be a hardened CCM, and the second portion 72 can be a non-hardened CCM. Alternatively still, the first portion 70 can be a hardened stainless steel. The second portion 72 can be a non-hardened stainless steel. In one example, the stainless steel can be 316L stainless steel. Alternatively still, the first portion 70 can be made of a first material, and the second portion 72 can be made of a second different material having a material hardness less than that of the first material. Thus, the first material can be non-hardened but still have a hardness greater than that of the second material. Alternatively still, the first portion 70 can be made of a first material and the second portion 72 can be made of a second material having a material hardness greater than the first material. However, the first portion 70 can be hardened, such that the hardened first material has a material hardness greater than the second material. The first and second materials can be chosen from any one of the materials listed above, or any suitable alternative material.

The first and second portions 70 and 72 are configured to attach to each other at a joint 73 so as to form the VA bone screw 43. Thus, the joint 73 can define an interface between the first and second portions 70 and 72. For instance, the first and second portions 70 and 72 can be welded to each other so as to define a weld joint 81, or attached to each other in accordance with any suitable alternative manner. In one example, one of the first portion 70 and the second portion 72 can define a projection 80, and the other of the first portion 70 and the second portion 72 can define a recess 82 that is configured to receive the projection 80. Thus, the joint 73 can include the projection 80 and the recess 82.

In one example, the first portion 70 can include the projection 80. The projection 80 can extend in a distal direction from the at least a portion of the head that is defined by the first portion 70. The projection 80 can be recessed radially inward toward the central screw axis 53 with respect to the outer surface 65 of the VA threaded head 59. In particular, the first portion 70 can define an instrument engagement member 86 that is configured to engage a driving instrument that drives the VA bone screw 43 to rotate about the central screw axis 53. The instrument engagement member 86 can define a socket, a cruciform, or any suitable alternative structure as desired. The instrument engagement member 86 can be defined by a proximal surface 71 of the first portion 70. The projection 80 can extend out in the distal direction from a distal surface 75 of the first portion 70 that is opposite the proximal surface 71. The projection 80 can be spaced radially inward from the outer surface 65. The projection 80 can define any cross section in a plane oriented normal to the central screw axis 53 as desired. For instance, the shape can be polygonal. Thus, the shape can be triangular, square, rectangular, or the like. Alternatively, the shape can be round as desired. It may be desirable for the shape to be non-circular in some examples.

The recess 82 can extend into a proximal surface 77 of the second portion 72. The proximal surface 77 can be disposed opposite the distal tip. The second portion 72 can include an outer wall 85 that includes an internal surface 83. The internal surface 83 can define the recess 82. In this regard, the proximal surface 77 of the second portion 72 and the distal surface 75 of the first portion 70 can partially define the joint 73. Further, the proximal surface 77 is configured to abut the distal surface 75 of the first portion 70 when the first and second portions 70 and 72 are attached to each other. The proximal surface 77 and the distal surface 75 can be disposed at the neck 74 of the VA locking bone screw 43 in one example. The projection 80 and the internal surface 83 can also partially define the joint 73. The recess 82 can extend into the second portion 72 along the distal direction, and can terminate in the second portion 72. Thus, in one example, the recess 82 does not extend entirely through the second portion 72. The recess 82 can extend centrally along the central screw axis 53. The recess 82 can define the same shape as the projection 80 in the plane oriented normal to the central screw axis 53. Further, the recess 82 can be entirely enclosed by the second portion 72 along the plane. Thus, an entirety of the internal surface 83 can be radially inwardly spaced from the outer surface 67 of the VA threaded shaft 47 in a direction toward the central screw axis 53.

During fabrication of the VA locking screw 43, the projection 80 can be aligned with the recess 82, and subsequently inserted into the recess 82. For instance, the first portion 70 can be moved in the distal direction with respect to the second portion 72 so as to insert the projection 80 into the recess 82. The projection 80 can thus be attached to the internal surface 83, thereby attaching the first portion 70 to the second portion 72. In one example, the recess 82 can be sized substantially equal to the projection, such that projection 80 can be press-fit to the internal surface 83 in the recess 82. In another example, the internal surface 83 and the projection 80 can be threaded and configured to threadedly mate with each other. Thus, the first and second portions 70 and 72 can threadedly engage each other so as to attach the first portion 70 to the second portion 72.

Additionally, the first and second portions 70 and 72 can be sealed to each other at the joint 73, which can prevent leakage of anatomical fluids into the joint 73 between the first and second portions 70 and 72, and can also enhance the strength of the joint. For instance, the projection 80 and the internal surface 83 can be sealed to each other. Further, the distal surface 75 of the first portion 70 and the proximal surface 77 of the second portion 72 can be sealed to each other. For instance, the projection can be glued to the internal surface 83. Further, the distal surface 75 of the first portion 70 can be glued to the proximal surface 77 of the second portion 72. Alternatively or additionally, the projection 80 can be welded to the internal surface 83. For instance, the projection 80 can be laser welded or electron beam welded to the internal surface 83. Further, the distal surface 75 of the first portion 70 can be welded to the proximal surface 77 of the second portion 72. For instance, the distal surface 75 of the first portion 70 can be laser welded or electron beam welded to the proximal surface 77 of the second portion 72. Alternatively or additionally still, the outer wall 85 can be radially crimped against the projection 73 to attach the first portion 70 to the second portion 72. For instance, the respective one of the first and second portions 70 and 72 that includes the outer wall 85 can define a crimp zone at an outer surface of the outer well 85 that is radially opposite the inner surface 83. The outer surface can, for instance, be unthreaded at the crimp zone.

With specific reference to FIG. 6A, it is recognized that the VA locking screw 43 can be constructed in a plurality of sizes. For instance, in one example, the VA locking screw can define any suitable outer diameter as desired, as defined by the outer diameter of the VA threaded shaft 47. The core diameter CD can be defined at the root of the at least one thread 69 of the VA threaded shaft 47. In one example, the outer diameter can range from approximately 2 mm to approximately 10 mm. For instance, in one example, the core diameter CD can be approximately 3.5 mm. In another example, the core diameter can be approximately 5 mm. It should be appreciated, of course, that the VA threaded shaft 47 can define any suitable alternative outer diameter as desired.

The projection 80 can further define any suitable size and shape as desired. In one example, the projection 80 can define any suitable maximum cross-sectional dimension DP along a plane that is oriented perpendicular to the central screw axis 53. The maximum cross-sectional dimension DP of the projection 80 can be configured as a diameter when the projection 80 is cylindrical. It is recognized, however, that the projection 80 can define any suitable cross-sectional shape as desired. In one example, the maximum cross-sectional dimension DP of the projection 80 can range from approximately 1.5 mm to approximately 3.7 mm. For instance, when the outer diameter CD is approximately 3.5 mm, the maximum cross-sectional dimension DP of the projection 80 can range from approximately 1.5 mm to approximately 2.2 mm. When the outer diameter CD is approximately 5 mm, the maximum cross-sectional dimension DP of the projection 80 can range from approximately 1.5 mm to approximately 3.7 mm.

Thus, it should be appreciated that the core diameter CD of the VA threaded shaft 47 and the maximum cross-sectional dimension DP of the projection 80 can define any suitable ratio as desired. For instance, the ratio can range from approximately 1.4 to approximately 3.3. For instance, when the outer diameter CD is approximately 3.5 mm, the ratio can range from approximately 1.6 to approximately 2.3. When the outer diameter is approximately 5 mm, the ratio can range from approximately 1.4 to approximately 3.3.

Further, the VA locking screw 43 can define any length L as desired. The length L can be measured along the central screw axis 53 from the proximal surface 71 of the first portion to the distal tip of the second portion 72. In one example, the length can range from approximately 10 mm to approximately 95 mm. For instance, when the outer diameter OT is approximately 5 mm, the length can range from approximately 14 mm to approximately 90 mm. When the outer diameter CD is approximately 3.5 mm, the length L can range from 10 mm to 95 mm. Further, the distal end of the projection 80 can be spaced from the end of the distal tip by any suitable distance as desired. For instance, the distance can be greater than 5 mm in one example. The above dimensions are provide as example only, it being appreciated that the VA locking screw 43 can define other sizes and shapes in accordance with the present disclosure. It has been found, however, that the above described dimensions can allow for the first and second portions 70 and 72 to reliably attach to each other while maintaining the overall strength of the VA locking screw 43.

Figure 6C:
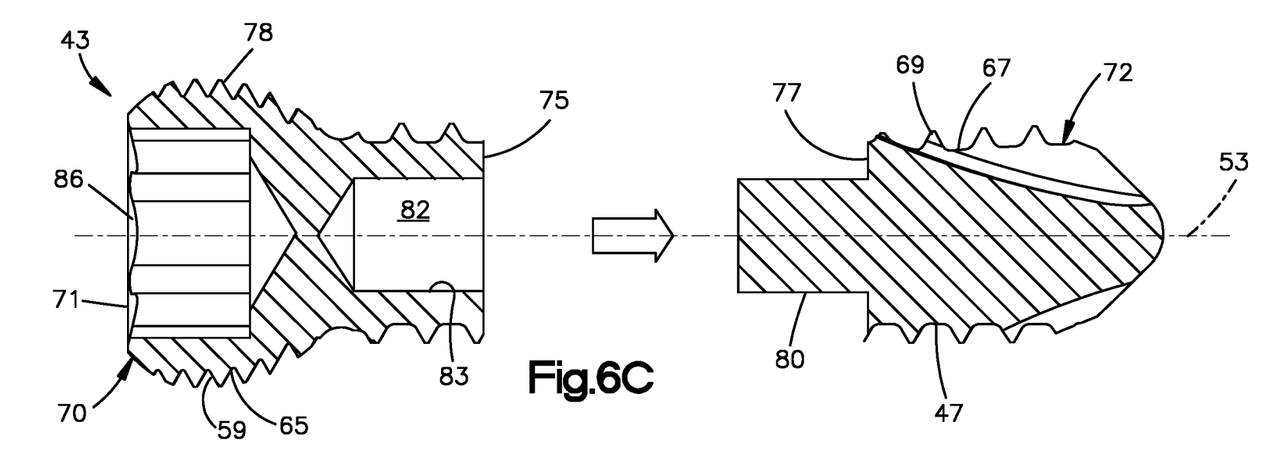
FIG. 6C is an exploded sectional side elevation view of the variable angle locking bone screw shown constructed in accordance with another example.

Referring now to FIG. 6C, in another example, the second portion 72 can include the projection 80. The projection 80 can extend in a proximal direction from the at least a portion of the shaft that is defined by the second portion 72. In particular, the projection 80 can extend out from the proximal surface 77 of the second portion 72 in the proximal direction. The proximal direction can be opposite the distal direction. The projection 80 can be recessed radially inward toward the central screw axis 53 with respect to the outer surface 67 of the VA threaded shaft 47.

The recess 82 can extend into the distal surface 75 of the first portion 70. In particular, the first portion 70 can include the outer wall 85 and the internal surface 83 that defines the recess 82. The recess 82 can extend into the first portion 70 along the proximal direction, and can terminate in the first portion 70. Thus, in one example, the recess 82 does not extend entirely through the first portion 70. The recess 82 can extend centrally along the central screw axis 53. The recess 82 can be entirely enclosed by the first portion 70 along a plane oriented normal to the central screw axis 53. Further, the recess 82 can be entirely enclosed by the first portion 70 along the plane. Thus, an entirety of the internal surface 83 can be radially inwardly spaced from the outer surface 65 of the VA threaded head 59 in a direction toward the central screw axis 53. The first and second portions 70 and 72 can be attached to each other and sealed to each other in the manner described above.

Figure 6D:
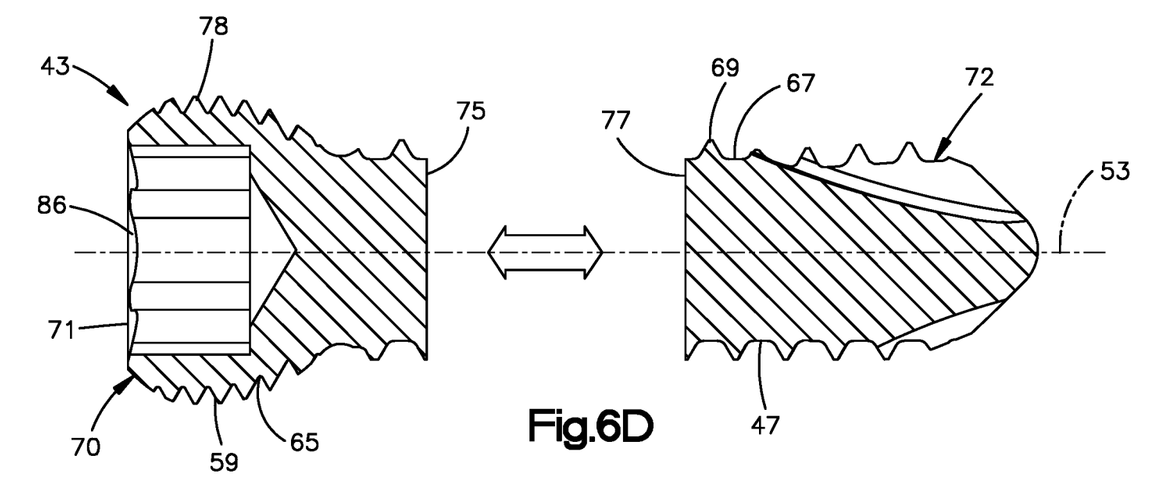
FIG. 6D is an exploded sectional side elevation view of the variable angle locking bone screw shown constructed in accordance with another example.

Referring now to FIG. 6D, in another example, the distal surface 75 of the first portion 70 and the proximal surface 77 of the second portion 72 can define substantially flat abutment surfaces. Thus, neither the first portion 70 nor the in the second portion 72 includes a defined projection or recess that mate to attach the first and second portions 70 and 72 to each other. In this example, the distal surface 75 and the proximal surface 77 can be brought into abutment with each other so as to define the joint. Further, at least a portion of the distal surface 75 and the proximal surface 77 can be friction-welded to each other to attach the first and second portions 70 and 72 to each other. For instance, the distal and proximal surfaces 75 and 77, respectively, can be friction welded to each other at the outer circumference of the bone screw. Thus, the friction weld can seal the first and second portions 70 and 72 to each other at the joint to prevent leakage of anatomical fluids between the first and second portions 70 and 72, and can also enhance the strength of the joint. In one example, the distal and proximal surfaces 75 and 77, respectively, can be friction welded to each other along their substantial entireties.

Referring now to FIGS. 6A-6D generally, the at least one thread 69 of the VA threaded shaft 47 can be formed in the outer surface 67 of the VA threaded shaft 47 after the first and second portions 70 and 72 have been attached to each other. Further, the at least one thread 78 of the VA threaded head 59 can be formed in the outer surface 65 after the first and second portions 70 and 72 have been attached to each other. Alternatively, the at least one thread 69 of the VA threaded shaft 47 can be formed in the outer surface 67 of the VA threaded shaft 47 prior to attaching the first and second portions 70 and 72 to each other. Further, the at least one thread 78 of the VA threaded head 59 can be formed in the outer surface 65 prior to attaching the first and second portions 70 and 72 to each other. The threads 69 and 78 can be formed by engaging any suitable cutting instrument with the outer surface 67 and 65, respectively, so as to cut into the respective outer surface.

As described above, the at least one thread 78 of the VA threaded head 59 can have a hardness greater than the at least one thread 69 of the VA threaded shaft 47. Further, the hardness of the at least one thread 78 of the VA threaded head 59 can be greater than the hardness of the at least one thread 46 of the bone plate 30, and thus the thread segments 60 of the threaded columns 50 (see FIG. 2A). For instance, the hardness of the at least one thread 78 of the VA threaded head 59 can be greater than the hardness of the entirety of the bone plate 30. Further, the hardness of the at least one thread 69 of the threaded shaft 47 can be less than or equal to the hardness of the at least one thread 46 of the bone plate 30, and thus the thread segments 60 of the threaded columns 50. For instance, the hardness of the at least one thread 69 of the threaded shaft 47 can be less than or equal to the hardness of the entirety of the bone plate 30. In one example, the plate 30, including the at least one thread 46, can be made from stainless steel, commercially pure titanium, TAN, or any suitable alternative material.

It is recognized that the at least one thread 78 of the VA threaded head 59 can be forced against the at least one thread 46 of the bone plate 30 as the VA threaded head 59 mates with the bone plate 30 inside the VA locking hole 54 at the oblique angle within the range of angles as described above. In this regard, it will be appreciated that the at least one thread 78 of the VA threaded head 59 can have a cantilever strength that is greater than the cantilever strength of the at least one thread 46 of the bone plate 30. This can be because the at least one thread 78 of the VA threaded head 59 has a hardness greater than the at least one thread 46 of the bone plate 30. Alternatively or additionally, in some examples, the geometry of the at least one thread 78 and the at least one thread 46 can have different geometries that impart an increased cantilever strength to the at least one thread 78 that is greater than the cantilever strength of the at least one thread 46 even when the material hardness of the at least one thread 78 is substantially equal to the material hardness of the at least one thread 46. Otherwise stated, the at least one thread 46 of the variable angle locking hole 54 can have a material hardness that is less than or equal to the hardness of the at least one thread 78, such that the at least one thread 78 of the variable angle threaded head 59 is configured to deform the at least one thread 46 of the variable angle locking hole 54 of the bone plate as the at least one thread 78 of the VA threaded head 59 mates with the at least one thread 46 of the variable angle locking hole 54.

Thus, when the VA locking screw 43 is mated to the bone plate 30 in the VA locking hole 54, the at least one thread 78 of the VA threaded head 59 can apply a force to the at least one thread 46 of the bone plate 30 that causes the at least one thread 46 of the bone plate 30 to deform, while the at least one thread 78 of the VA threaded head 59 does not deform. Otherwise stated, the thread segments 60 that are purchased with the VA threaded head 59 can undergo a slight elastic and/or plastic deformation at their respective roots when the harder VA threaded head 59 is locked in the softer VA locking hole 54. The form fit can increase the reliability of purchase between the VA locking screw 43 and the bone plate 30 in the VA locking hole 54. Further, because the VA threaded shaft 47 is non-hardened, the VA threaded shaft 47 has a desirable fatigue strength that would be reduced if the threaded shaft was hardened.

Referring now to FIGS. 7A-7C, the bone plate 30 can include any suitable fixation hole that is configured to mate with the VA locking screw 43 at any of the angles within the range of angles described above. For instance in one example, the bone plate 30 can include a combination hole 90 that includes both the VA locking hole 54 and the compression hole 52. Thus, the internal surface 39 of the combination hole 90 can define both the VA locking hole 54 and the compression hole 52. The VA locking hole 54 and the compression hole 52 of the combination hole 90 can be open to each other along a direction that is perpendicular to one or both of the central hole axis 45 of the VA locking hole 54 and the central hole axis 45 of the compression hole 52. The central hole axis 45 of the VA locking hole 54 and the compression hole 52 of the combination hole 90 can be aligned with each other along the longitudinal L and thus along the central axis of the bone plate 30, or along any suitable alternative direction as desired.

The internal surface 39 of the bone plate 30 can thus also define the compression surface 57 of the compression hole 52 of the combination hole 90. In one example, the compression surface 57 can be concave in the axial direction with respect to the central hole axis 45 of the compression hole 52. For instance, the compression surface 57 can be dish shaped or spherical. Thus, the compression surface 57 can be configured to be placed in surface contact with the compression head 58 of the compression screw 49. Alternatively, the compression surface 57 can be linear in the axial direction as it tapers radially inwardly toward the central hole axis 45.

During operation, the shaft 35 of the compression screw 49 can be inserted through the compression hole 52 of the combination hole 90 and driven into the underlying bone 22 as described above. For instance, the compression screw 49 can be inserted into the compression hole 52 such that the central screw axis 53 is oriented at any angle with respect to the central hole axis 45 within the range of angles described above. Rotation of the compression screw 49 while the shaft 35 is threadedly purchased with the underlying bone 22 causes the compression head 58 to bear against the compression surface 57, and thus the internal surface 39, so as to apply a compression force to the bone plate 30 that, in turn, becomes compressed against the underlying bone 22.

Thus, it should be appreciated that the combination hole 90 is configured to selectively receive the compression screw 49, the VA locking screw 43 described above and the standard-type locking screw 51 in the manner described above. The internal surface 39 of the combination hole 90 can define a neck 92 at an interface between the VA locking hole 54 and the compression hole 52. Thus, it can be said that the VA locking hole 54 is open to the compression hole 52. Two of the columns 50 of the VA locking hole 54 of the combination hole 90 can extend circumferentially to the neck 92. The recess 48 between the two of the columns 50 can thus extend into the compression hole 52. The VA locking hole 54 of the combination hole 90 can be otherwise as described above.

It should be appreciated that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should be further appreciated that the various alternative embodiments described above with respect to one illustrated embodiment can apply to all embodiments as described herein, unless otherwise indicated.

What is claimed:

1. A variable angle bone screw that extends along a central screw axis, the variable angle bone screw comprising:
    a first portion defining at least a portion of a head having at least one external thread configured to mate with a thread of a variable angle locking hole of a bone plate when the central screw axis is oriented at any one of a plurality of angles within a range of angles with respect to a central axis of the variable angle locking hole at which the head is configured to threadedly mate with the thread of the variable angle locking hole; and a second portion defining at least a portion of a shaft having at least one thread configured to purchase with bone, wherein the at least one thread of the first portion has a first material hardness, the at least one thread of the second portion has a second material hardness less than the first material hardness, and the second portion is separate from the first portion and attached to the first portion at a joint, wherein the first portion comprises a material that is hardened, and the second portion comprises the material of the first portion, except that the material of the second portion is non-hardened.

2. The variable angle bone screw as recited in claim 1, wherein one of the first and second portions defines a projection, and the other of the first and second portions defines a recess configured to receive the projection so as to attach the first portion to the second portion.

3. The variable angle bone screw as recited in claim 2, wherein the first and second portions define substantially flat abutment surfaces that are friction-welded to each other so as to attach the first portion to the second portion.

4. The variable angle bone screw as recited in claim 2, wherein the projection is at least one of threaded and press-fit in the recess so as to attach the first portion to the second portion.

5. The variable angle bone screw as recited in claim 2, wherein the one of the first and second portions that defines the recess comprises an outer wall defining an internal surface that, in turn, at least partially defines the recess, and the outer wall is crimped to the projection so as to attach the first portion to the second portion.

6. The variable angle bone screw as recited in claim 1, wherein a distal surface of the first portion abuts a proximal surface of the second portion when the first and second portions are attached to each other, and wherein the distal and proximal surfaces are sealed to each other.

7. The variable angle bone screw as recited in claim 5, wherein the proximal and distal surfaces are one of welded and glued to each other.

8. The variable angle bone screw as recited in claim 7, wherein the proximal and distal surfaces are laser welded, electron beam welded, or friction welded to each other.

9. The variable angle bone screw as recited in claim 1, wherein the first portion comprises one of TAN, 316L, TAV, and CCM that is hardened, and the second portion comprises the same one of TAN, 316L, TAV, and CCM that is non-hardened.

10. The variable angle bone screw as recited in claim 1, wherein the first and second portions comprise different materials.

11. The variable angle bone screw as recited in claim 1, wherein the at least one thread of the head defines a peak that lies on one of a conical path and a spherical path.

12. The variable angle bone screw as recited in claim 2, wherein the first portion comprises the projection and the second portion defines the recess.

13. The variable angle bone screw as recited in claim 2, wherein the shaft defines a core diameter, the projection defines an outer cross-sectional dimension, and the core diameter and outer cross-sectional dimension define a ratio that ranges from approximately 1.4 to approximately 3.3.

14. The variable angle bone screw as recited in claim 2, wherein the first portion defines the recess, and the second portion comprises the projection.

15. A bone fixation system comprising:
the variable angle bone screw as recited in claim 1; and
the plate recited in claim 1, wherein the thread of the variable angle locking hole has a material hardness that is less than or equal to the first material hardness, such that the thread of the head is configured to deform the thread of the variable angle locking hole of the bone plate as the thread of the head mates with the thread of the variable angle locking hole.

16. The bone fixation system as recited in claim 15, wherein the thread of the variable angle locking hole defines a plurality of threaded columns circumferentially spaced from each other.

* * * * *